US 6,555,098 B1

(12) United States Patent
Murphy et al.

(10) Patent No.: US 6,555,098 B1
(45) Date of Patent: Apr. 29, 2003

(54) COSMETIC DEODORANT PRODUCTS CONTAINING ENCAPSULATED BICARBONATE AND FRAGRANCE INGREDIENTS

(75) Inventors: Richard T. Murphy, Belle Mead, NJ (US); Wolfgang R. Bergmann, Princeton, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 1753 days.

(21) Appl. No.: 08/605,651

(22) Filed: Feb. 22, 1996

Related U.S. Application Data

(63) Continuation of application No. 08/354,235, filed on Dec. 9, 1994.

(51) Int. Cl.$^7$ .................................................. A61K 7/32
(52) U.S. Cl. ..................... 424/65; 424/493; 424/497; 424/722; 424/717; 428/402.24
(58) Field of Search .................. 424/65, 493, 497, 424/722, 717; 428/402.24

(56) References Cited

U.S. PATENT DOCUMENTS

| | | | | |
|---|---|---|---|---|
| 4,919,934 A | * | 4/1990 | Deckner | 424/401 |
| 5,354,556 A | | 10/1994 | Sparks et al. | 424/419 |
| 5,354,559 A | | 10/1994 | Morehouse | 424/488 |
| 5,354,737 A | | 10/1994 | Barr et al. | 512/17 |
| 5,376,362 A | * | 12/1994 | Murphy | 424/66 |

* cited by examiner

*Primary Examiner*—Evelyn Mei Huang
(74) *Attorney, Agent, or Firm*—Stephen B. Shear

(57) ABSTRACT

This invention provides deodorant and deodorant-antiperspirant cosmetic stick and roll-on products with an organic matrix having a dispersed phase of discrete particles of an encapsulated bicarbonate salt such as sodium bicarbonate, and discrete particles of an encapsulated fragrance compound such as musk ketone. The particle surfaces are coated with a polymer such as maltodextrin starch. When this type of cosmetic product is applied to underarm surfaces, the deodorizing activity is signaled by the release of a fragrance aroma.

15 Claims, No Drawings

COSMETIC DEODORANT PRODUCTS CONTAINING ENCAPSULATED BICARBONATE AND FRAGRANCE INGREDIENTS

This application is a continuation of application Ser. No. 08/354,235, filed Dec. 9, 1994.

BACKGROUND OF THE INVENTION

Alkali metal bicarbonate is a commodity reagent which has found application in a broad variety of products such as laundry detergents, deodorizers, creams and lotions, dentifrices, antacids, buffers, fungicides, and the like.

The inclusion of particulate alkali metal bicarbonate in a cosmetic deodorant stick or roll-on formulation provides a product with improved deodorant properties. Dimensional instability of a cosmetic stick or roll-on product containing bicarbonate ingredient, and the esthetic appearance and the "feel" on the skin, are among the difficulties encountered in the preparation of a low residue cosmetic antiperspirant-deodorant product. The high density of a suspended particle-phase of bicarbonate ingredient relative to the low density of an organic matrix phase contributes to the instability and settling of the bicarbonate particle phase in a cosmetic stick or roll-on personal care product.

In addition, a bicarbonate ingredient often is incompatible with the active astringent salts and with other ingredients of conventional cosmetic stick products. A bicarbonate ingredient in direct contact with acidic ingredients is susceptible to decomposition into carbon dioxide and water.

An additional factor is the risk of a fragrance ingredient incompatibility with bicarbonate and astringent ingredients.

There is continuing interest in the development of reagents such as alkali metal bicarbonate and ammonium bicarbonate which have a uniform fine grain particle size, and exhibit a novel combination of properties when utilized as an ingredient in personal care, biologically active, household, and specialty type products. There is also interest in the development of a bicarbonate powder which is in a form that is stable when blended with an acidic ingredient in a formulation.

Accordingly, it is an object of this invention to provide an alkali metal bicarbonate or ammonium bicarbonate powder which has a fine grain particle size, and which is free-flowing and essentially free of agglomerated solids.

It is another object of this invention to provide an encapsulated powder composition that is a blend of particles which are composed of polymer-coated crystallites of bicarbonate salt and fragrance compounds, and which have a lower density than the inner core bicarbonate crystallites of the encapsulated particles.

It is a further object of this invention to provide a cosmetic deodorant product which, when applied to underarm surfaces, signals deodorizing activity by the release of a fragrance aroma.

Other objects and advantages of the present invention shall become apparent from the accompanying description and examples.

DESCRIPTION OF THE INVENTION

One or more objects of the present invention are accomplished by the provision of an encapsulated bicarbonate salt powder composition comprising (1) discrete crystallites of at least one ingredient selected from alkali metal and ammonium bicarbonates, and (2) between about 0.1–20 weight percent of discrete crystallites of a fragrance ingredient; wherein the crystallites are in the form of surface-coated particles.

The bicarbonate salt crystallites can have an average particle size between about 5–150 microns. The fragrance crystallites can have an average particle size between about 5–300 microns. A preferred range for both bicarbonate and fragrance crystallites is an average particle size between about 5–80 microns. A present invention encapsulated powder composition typically is free-flowing and essentially free of agglomerated solids.

The term "discrete" as employed herein refers to crystallites which are individually distinct solids.

The term "average particle size" as employed herein refers to the average of the largest dimension of particles.

The particulate bicarbonate salt starting material of an invention encapsulated powder composition is selected from alkali metal and ammonium bicarbonates, such as sodium bicarbonate, potassium bicarbonate and ammonium bicarbonate, and mixtures thereof.

The particulate fragrance starting material preferably is selected from crystalline organic compounds which include vanillin, ethyl vanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, proeugenol acetate, evernyl, and the like.

Other suitable fragrances such as menthol and camphor exhibit kinesthetic properties, and are utilized in personal products to provide a "cod feel" on skin surfaces.

The polymer coating on the ingredient crystallites can be applied to the bicarbonate powder and fragrance powder starting materials in separate procedures, and the two encapsulated powders then can be blended in a selected proportion of ingredients.

In an alternative procedure, the bicarbonate and fragrance powders are pre-blended, and the polymer coating is applied to the powder blend. Depending on the type of polymer and the coating conditions, and the particle size of the bicarbonate and fragrance crystallites, the final encapsulated powder composition can have a content of 10 weight percent or higher of encapsulated particles having a core content of both bicarbonate and fragrance crystallites. During the polymer coating procedure, crystallites with a liquid surface coating can make contact and coalesce into larger encapsulated particles with a content of multiple crystallites.

The application of the polymer coating to the ingredient crystallite surfaces is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the crystallites, the solvent medium is removed by evaporation, thereby forming a continuous film coating which encapsulates the discrete fine grain crystallites.

In a preferred coating procedure, bicarbonate powder is dispersed in an aqueous medium which contains a coating polymer ingredient. The aqueous dispersion is atomized and sprayed into heated air to remove the aqueous phase, and to provide a free-flowing polymer-encapsulated bicarbonate powder product.

The coating thickness on the crystallite surfaces typically will vary in the range between about 0.1–20 microns. The coating can consist of a single layer or multiple layers. The polymeric coating can constitute between about 5–70 weight percent of the total dry weight of the coated crystallites.

A polymer employed for coating the bicarbonate and fragrance crystallites is selected from hydrophilic organic polymers and hydrophobic (water-insoluble) organic polymers and mixtures thereof.

A hydrophilic polymer employed for coating the ingredient crystallites is selected from water-soluble and water-dispersible organic polymers. A mixture of polymers can be employed, and a content of between about 0.5–40 weight percent of a water-insoluble polymer, based on the coating weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating ingredient crystallites include gum arabic, gum karaya, gum tragacanth, guar gum, locust bean gum, xanthan gum, carrageenan, alginate salt, casein, dextran, pectin, agar, sorbitol, 2-hyroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating ingredient crystallites include polyvinyl acetate, polyacrylamide, polyvinyl chloride, polystyrene, polyethylene, polyurethane, and the like.

For purposes of release of the core matrix bicarbonate salt and fragrance ingredients in the encapsulated particles when introduced into an aqueous environment, a surface coating of water-insoluble polymer preferably has a content between about 5–30 weight percent of a particulate water-extractable organic or inorganic filler, such as sodium bicarbonate, sodium carbonate, sodium chloride, calcium chloride, monosaccharide or disaccharide, sorbitol, mannitol, and the like.

The rate of release of bicarbonate salt and fragrance core matrix content of the particles under moisture conditions can be controlled by the quantity and type of polymer coating on the particle surfaces.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an intermediate rate when in contact with underarm type of moisture.

In another embodiment this invention provides a cosmetic deodorant product comprising a liquid, semi-solid or solid organic matrix which contains between about 0.5–20 weight percent, based on the product weight, of an encapsulated powder composition homogeneously dispersed therein, wherein the encapsulated powder composition comprises (1) discrete crystallites of at least one ingredient selected from alkali metal and ammonium bicarbonates, and (2) between about 0.1–20 weight percent of discrete crystallites of a fragrance ingredient; and wherein the crystallites are in the form of polymer surface-coated particles.

A present invention cosmetic stick or roll-on deodorant product can contain between about 5–25 weight percent of an antiperspirant compound as an additional ingredient.

A present invention cosmetic stick product can consist of a solid organic matrix comprising the following parts by weight of ingredients:

| | |
|---|---|
| volatile oil | 10–55 |
| liquid emollient | 1–35 |
| low melting point wax | 12–30 |

The solid organic matrix has homogeneously dispersed therein between about 0.5–20 weight percent, based on the product weight, of an encapsulated powder composition as described hereinabove.

An invention antiperspirant-deodorant cosmetic stick product typically contains the following weight proportions of main ingredients:

| Ingredient | Weight |
|---|---|
| volatile oil | 25–50 |
| liquid emollient | 2–20 |
| wax (MP 95°–180° F.) | 15–20 |
| antiperspirant | 20–28 |
| encapsulated bicarbonate/fragrance powder | 0.1–25 |
| surfactant | 1–3 |

The volatile oil ingredient preferably is selected from silicone and branched-chain hydrocarbon compounds.

A volatile silicone oil ingredient in a cosmetic stick or roll-on product of the present invention preferably is a cyclic or linear polydimethylsiloxane containing between about 3–9 silicon atoms. A suitable cyclic volatile polydimethylsiloxane compound is illustrated by the formula:

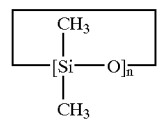

where n is an integer with a value of about 3–7.

A suitable linear polydimethylsiloxane is illustrated by the formula:

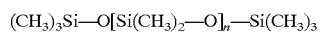

where n is an integer with a value of about 1–7.

Linear volatile silicone compounds generally have viscosities of less than about centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. CTFA Cosmetic Ingredient Dictionary, Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Parmethyl 101A and Permethyl 102A.

The liquid emollient ingredient of an invention cosmetic stick or roll-on product is selected from one or more water-insoluble organic compounds which are liquid at 25° C. and which contribute a combination of properties that are advantageous in an invention cosmetic stick or roll-on product.

The term "water-insoluble" as employed herein refers to an emollient ingredient which has a water-solubility of less than about one gram per 100 grams of water at 25° C.

A present invention emollient ingredient exhibits a low degree of irritation and toxicity in topical applications, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters of $C_9$–$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°–180° F.

Suitable types of wax-like compounds include fatty acids, fatty alcohols, fatty acid esters, fatty acid amides, and the like, which have an aliphatic chain length between about 8–30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°–220° F. Illustrative of these higher melting waxes are beeswax, spermaceti, carnauba, bayberry, candelilla, montan, ozokerite, ceresin, paraffin, castor wax, Fischer-Tropsch waxes, and the like.

The antiperspirant ingredient of a present invention cosmetic stick or roll-on product typically is a particulate astringent compound which has an average particle size between about 1–100 microns. Superior cosmetic stick properties are obtained if part or all of the antiperspirant ingredient is in the form of particles which have a diameter less than about one micron. Optionally, the antiperspirant ingredient can be pre-coated with a polymer to prevent interaction with the other ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium trichlorohydrex glycine. Aluminum-zirconium tetrachlorohydrex glycine is commercially available as Rezal 36 GP Superultrafine (Reheis), and Reach AZP 908 (Reheis).

Optional ingredients also may be included in an invention cosmetic formulation, such as bacteriostats, fungistats, fillers, stabilizing agents, antioxidants, pigments, coloring agents, perfumes, chelating agents, and the like.

A surfactant ingredient of an invention cosmetic formulation is selected from nonionic, cationic and anionic polymers. Suitable surfactant polymers include cetyltrimethylammonium bromide; sodium lauryl sulfate; sodium dodecylbenzene-sulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

A bacteriostat such as 2,4,4'-trichloro-2'-hydroxydiphenyl ether (Triclosan) typically is added in a quantity between about 0.08–3 weight percent, based on the weight of the cosmetic stick or roll-on product.

In another embodiment this invention provides a cosmetic roll-on product consisting of a liquid organic matrix comprising the following parts by weight of ingredients:

| | |
|---|---|
| Volatile oil | 55–70 |
| liquid emollient | 3–10 | and the liquid organic matrix has homogeneously dispersed therein about 0.5–20 parts by weight, based on the product weight, of an encapsulated powder composition comprising (1) discrete crystallites of at least one ingredient selected from alkali metal and ammonium bicarbonates, and (2) between about 0.1–20 weight percent of discrete crystallites of a fragrance ingredient; wherein the crystallites are in the form of polymer surface-coated particles.

In another embodiment this invention provides a method of practicing personal hygiene which comprises applying a present invention cosmetic stick or roll-on product to underarm surfaces in a deodorant-effective amount, wherein the initiation and continuation of deodorizing activity is signaled by an organoleptic fragrance aroma.

A significant advantage of the present invention cosmetic formulation is the signaling of deodorizing activity by a sensible aroma of fragrance which is released after underarm application of the cosmetic formulation. After application, underarm moisture initiates a continuous release of bicarbonate salt deodorant and fragrance from the polymer-coated particles of encapsulated bicarbonate and fragrance crystallites.

Other advantages are provided by the practice of the present invention. As noted in the Background section of the specification, the relative densities of the liquid and solid phases in a cosmetic stick or roll-on product directly affects the stability and esthetics of the formulations.

Density matching of inorganic and organic phases is a significant factor in cosmetic stick and roll-on products. The present invention formulations contain a polymer-coated bicarbonate deodorant ingredient of lower density which more closely matches the density of the organic matrix of a cosmetic stick or roll-on product than does uncoated bicarbonate ingredient.

When there is density matching of organic matrix and dispersed polymer-coated bicarbonate particle phases, a cosmetic stick or roll-on product has improved dimensional stability, and better esthetic appearance and "feel" when applied to human skin.

In general, the ingredients of a cosmetic formulation can be blended in any order. However, in the practice of the invention process for cosmetic stick manufacture there is advantage in utilizing a phased order of ingredient addition and blending under controlled temperature conditions. Additional advantage is obtained in the invention process if there is a minimal time lapse between the alkali metal bicarbonate deodorant ingredient addition step and the cosmetic stick container filling and solidifying step. Alkali metal bicarbonate can convert to alkali metal carbonate, carbon dioxide and water at elevated temperatures.

Adding the encapsulated bicarbonate salt as the last ingredient of the blended formulation, and processing the formulation to the solid cosmetic stick formation stage within a short time period, are factors which minimize the degradation of the bicarbonate salt ingredient, and the undesirable formation of water and carbon dioxide vapor byproducts. The addition and mixing of the bicarbonate salt ingredient into the formulation, and the dispensing of the formulation into cosmetic stick containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of the invention process for the production of a cosmetic stick product can be conducted in conventional equipment, and is readily adaptable to a commercial-scale manufacturing operation.

A present invention cosmetic stick product preferably has a hardness penetration value between about 4–12 millimeters, as determined by American Society For Testing Materials (ASTM) Method D5.

A present invention antiperspirant-deodorant cosmetic stick or roll-on product has exceptional properties for treating or preventing perspiration and malodor associated with human underarm perspiration. A present invention cosmetic formulation can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates a fluidized bed procedure for coating particulate bicarbonate and fragrance compounds with a hydrophilic polymer in accordance with the present invention.

A fluidized bed vessel is utilized which is equipped with a Wurster air-suspension coater system (WARF) as described in U.S. Pat. Nos. 4,568,559 and 4,877,621.

A coating solution is prepared by dissolving pblyethylene glycol (45 g, Poly-G 2000, Olin Corp.), and propylene glycol butyl ether (10 g, PPG 14, Americol) in ethanol (500 g)/water (75 g).

Sodium bicarbonate is utilized as one of the core matrix type of crystallites. The sodium bicarbonate (Particle Size Technology, Inc.) has an average particle size of about 5 microns, and 90 percent of the particles have a diameter less than 20 microns.

Cedrol (Fermenich) is utilized as the second of the core matrix type of crystallites. The musk ketone powder is pulverized to an average particle size of about 30 microns.

The sodium bicarbonate powder is blended with 12 weight percent of cedrol powder. The blended powder is charged into the coating chamber of the coater system.

Compressed air is introduced into the coating chamber, and the polymeric coating solution is sprayed on the air-suspended bicarbonate and musk ketone crystallites, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that maltodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.)

The procedure is repeated except that an 80/20 by weight mixture of polyvinylpyrrolidone/polyvinyl acetate is employed as the crystallite-coating polymer ingredient.

The coated particles consist of a polymer coating on an inner core of a single crystallite or multiple crystallites.

EXAMPLE II

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
| --- | --- |
| Lanette 18 DEO[1] | 175.00 |
| Castorwax MP-80[2] | 31.25 |
| ICI G-2162[3] | 6.25 |

[1]Stearyl alcohol; Henkel.
[2]Hydrogenated castor oil; RTD.
[3]PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum-zirconium tetrachlorohydrex glycine (312.50 lbs, Reheis) are added. The temperature is maintained at 176° F. for about 40 minutes until the fluid medium is uniform, and then the temperature is lowered to 154° F.

A blended polymer-coated sodium bicarbonate/fragrance powder (148 lbs.) is added with stirring to Silicone oil DC 245 (200 lbs, Dow Corning) in a second mixing tank at a temperature of 154° F. to form a homogeneous suspension medium. The blend of sodium bicarbonate and 5 weight percent of maple lactone (Firmenich) powders are pre-coated with amylodextrin employing a fluidized bed type procedure as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

EXAMPLE III

This Example illustrates a precipitation procedure for forming crystallites of potassium bicarbonate, and coating the bicarbonate crystallites and fragrance crystallites with a hydrophilic polymer in accordance with the present invention.

A coating solution is prepared by dissolving polyethylene glycol (10 g, Poly-G 2000, Olin Corp.), propylene glycol butyl ether (5 g, PPG 14, Americol), and polyoxyethylene-sorbitan monolaurate (1.0 g; Tween 20; ICI Americas, Inc.) in 1-propanol (300 g).

A solution of potassium bicarbonate (30 g) in water (100 g) is prepared. A 2 gram quantity of coumarin powder (average particle size of 30 microns) is suspended in the aqueous solution. The suspension medium then is added dropwise to the coating solution with high speed stirring.

The admixture which forms is a suspension of potassium bicarbonate and coumarin crystallites in the liquid medium. The liquid medium is concentrated to dryness by removal of water/1-propanol azeotrope under vacuum at 60° C. in a rotating evaporator.

The resultant dry powder is composed of particles which consist of a 33% by weight coating on an inner core of single and multiple crystallites of potassium bicarbonate and coumarin. The potassium bicarbonate crystallites have particle size distribution substantially in the range of 1–30 microns.

EXAMPLE IV

This Example illustrates the preparation of an antiperspirant-deodorant roll-on product in accordance with the present invention.

A roll-on formulation is prepared by blending the following proportions of ingredients:

| | lbs. |
|---|---|
| Silicone oil DC 245 | 60.90 |
| Quaternium-18 hectorite clay (Rheox) | 9.50 |
| Reach AZP 908 | 23.00 |
| Encapsulated potassium bicarbonate[1] | 6.00 |

-continued

| | lbs. |
|---|---|
| Cab-o-Sil fumed silica (Cabot) | 0.60 |
| Propylene carbonate | 0.50 |

[1]Prepared by an Example I type of fluidized bed procedure. A powder blend of potassium bicarbonate/ethylvanillin (94/6 weight ratio) is encapsulated with amylodextrin starch.

The roll-on formulation exhibits excellent dimensional stability when packaged and maintained under storage conditions for six months.

What is claimed is:

1. A cosmetic deodorant product comprising an organic matrix which contains between about 0.5–20 weight percent of an encapsulated powder composition homogeneously dispersed therein, wherein the encapsulated powder composition comprises (1) discrete crystallites of at least one ingredient selected from alkali metal and ammonium bicarbonates, and (2) between about 0.1–20 weight percent of discrete crystallites of a fragrance ingredient; wherein the crystallites are in the form of polymer surface-coated particles, and the crystallite ingredients have an average particle size in the range between about 5–80 microns; and wherein at least about 10 weight percent of the encapsulated particles have a core content of both bicarbonate and fragrance crystallites.

2. A cosmetic deodorant product in accordance with claim 1 which is a cosmetic stick or roll-on formulation.

3. A cosmetic stick product consisting of a solid organic matrix comprising the following parts by weight of ingredients:

| | |
|---|---|
| volatile oil | 10–55 |
| liquid emollient | 1–35 |
| low melting point wax | 12–30 | and the solid organic matrix contains between about 0.5–20 weight percent of an encapsulated powder composition homogeneously dispersed therein, wherein the encapsulated powder composition comprises (1) discrete crystallites of at least one ingredient selected from alkali metal and ammonium bicarbonates, and (2) between about 0.1–20 weight percent of discrete crystallites of a fragrance ingredient; and wherein the crystallites are in the form of polymer surface-coated particles, and the crystallite ingredients have an average particle size in the range between about 5–80 microns.

4. A cosmetic stick product in accordance with claim 3 wherein the volatile oil ingredient comprises a cyclic or linear polydimethylsiloxane containing 3–9 silicon atoms.

5. A cosmetic stick product in accordance with claim 3 wherein the volatile oil ingredient comprises a $C_{12}$–$C_{20}$ branched-chain hydrocarbon.

6. A cosmetic stick product in accordance with claim 3 wherein the liquid emollient ingredient is a water-insoluble organic acid, ester or ether compound.

7. A cosmetic stick product in accordance with claim 3 wherein the wax ingredient is selected from $C_8$–$C_{30}$ alcohol, acid, ester and amide compounds.

8. A cosmetic stick product in accordance with claim 3 wherein the encapsulated bicarbonate crystallites are sodium, potassium or ammonium bicarbonate or any mixture thereof.

9. A cosmetic stick product in accordance with claim 3 which has a content between about 0.05–10 weight percent of a biocidal ingredient.

10. A cosmetic stick product in accordance with claim 3 which contains between about 5–25 weight percent of an antiperspirant compound as an additional ingredient.

11. An encapsulated bicarbonate salt powder composition comprising (1) discrete crystallites of at least one ingredient selected from alkali metal and ammonium bicarbonates, and (2) between about 0.1–20 weight percent of discrete crystallites of a fragrance ingredient; wherein the crystallites are in the form of polymer surface-coated particles, and the crystallite ingredients have an average particle size in the range between about 5–80 microns: and wherein at least about 10 weight percent of the encapsulated particles have a core content of both bicarbonate and fragrance crystallites.

12. An encapsulated powder composition in accordance with claim 11 wherein the encapsulated bicarbonate particles are sodium, potassium or ammonium bicarbonate or any mixture thereof.

13. An encapsulated powder composition in accordance with claim 11 wherein the fragrance ingredient is an organic compound selected vanillin, ethyl vanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, isoeugenol acetate and evernyl.

14. An encapsulated powder composition in accordance with claim 11 wherein the polymer surface coating on the particles comprises between about 5–70 weight percent of the dry particle weight.

15. An encapsulated powder composition in accordance with claim 11 wherein the surface coating on the particles is a hydrophilic polymer or a water-insoluble polymer or a mixture thereof.

* * * * *